United States Patent
Zou et al.

(10) Patent No.: US 11,572,505 B1
(45) Date of Patent: Feb. 7, 2023

(54) FLASH-TYPE CHEMILUMINESCENCE SYSTEM BASED ON CUINS2@ZNS NANOMATERIAL

(71) Applicant: SHANDONG UNIVERSITY, Jinan (CN)

(72) Inventors: Guizheng Zou, Jinan (CN); Shuangtian Dong, Jinan (CN)

(73) Assignee: SHANDONG UNIVERSITY, Jinan (CN)

( * ) Notice: Subject to any disclaimer, the term of this patent is extended or adjusted under 35 U.S.C. 154(b) by 0 days.

(21) Appl. No.: 17/663,779

(22) Filed: May 17, 2022

(51) Int. Cl.
| | |
|---|---|
| *G01N 21/76* | (2006.01) |
| *G01N 33/58* | (2006.01) |
| *C09K 11/58* | (2006.01) |
| *C09K 11/00* | (2006.01) |
| *C09K 11/62* | (2006.01) |
| *B82Y 15/00* | (2011.01) |
| *B82Y 20/00* | (2011.01) |
| *C09K 11/54* | (2006.01) |

(52) U.S. Cl.
CPC ............ *C09K 11/588* (2013.01); *C09K 11/54* (2013.01); *C09K 11/623* (2013.01); *G01N 21/76* (2013.01); *G01N 33/588* (2013.01)

(58) Field of Classification Search
None
See application file for complete search history.

(56) References Cited

FOREIGN PATENT DOCUMENTS

| | | |
|---|---|---|
| CN | 104449697 A | 3/2015 |
| CN | 111944521 A | 11/2020 |
| CN | 112940719 A | 6/2021 |

OTHER PUBLICATIONS

Fu et al. (Promising electrochemiluminescence from . . . Analytical Chem., vol. 91, Jul. 12, 2019, pp. 10221-10226 (Year: 2013).*
Liu et al. (A visual electrochemiluminescence biosensor . . . , Analytical and Bioanalytical Chem., vol. 412, Feb. 3, 2020, pp. 1893-1899 (Year: 2020).*

(Continued)

*Primary Examiner* — Neil N Turk
(74) *Attorney, Agent, or Firm* — CBM Patent Consulting, LLC

(57) ABSTRACT

A $CuInS_2$@ZnS nanomaterial synthesized with thiosalicylic acid and sodium citrate as dual-stabilizers is taken as a chemiluminescent luminophore, and Tris buffer containing both $N_2H_4 \cdot H_2O$ and $H_2O_2$ is taken as the triggering solution; introducing the $H_2O_2$ into the triggering solution can bring out greatly enhanced CL emission and obviously shortened CL process, enable the $CuInS_2$@ZnS nanomaterial with strong flash-type and near-infrared CL; the luminophore of $CuInS_2$@ZnS nanomaterial is synthesized by a one-pot method; compared with acridinium ester (a classical flash-type chemiluminescent substance), the $CuInS_2$@ZnS nanomaterial is simple in synthesis method, mild in conditions and short in the required time, the synthesized $CuInS_2$@ZnS nanomaterial is not easy to decompose under light, and the CL waveband is in the near-infrared region.

8 Claims, 9 Drawing Sheets

(56) References Cited

OTHER PUBLICATIONS

Long et al. (Near-infrared electrochemiluminescence from non-toxic . . . , Journal of Materials Chemistry C, vol. 5, Nov. 14, 2017 , pp. 12393-12399 (Year: 2017).*
Rasoulzadeh et al. A highly sensitive chemiluminescence assay . . . , Microchemical Journal, vol. 159, Jul. 23, 2020, pp. 1-5 (Year: 2020).*
Shu Qunwei, et al. Shape-controlled synthesis of star-shaped Cu2-xSySe1-y materials with highly enhanced chemiluminescence. Journal of Alloys and Compounds, vol. 678 Journal of Alloys and Compounds, vol. 678, p. 70-79 Jun. 1, 2016.
Li Zhipeng, et al. Hydrazine hydrate and dissolved oxygen-triggered near-infrared chemiluminescence from CuInS2@ZnS nanocrystals for bioassays. Analytical Chemistry, vol. 93, Issue 25, p. 8931-39 Jun. 17, 2021.

* cited by examiner

FLASH-TYPE CHEMILUMINESCENCE SYSTEM BASED ON CUINS2@ZNS NANOMATERIAL

CROSS REFERENCES

This application claims priority to Chinese Patent Application Ser. No. CN2021109738745 filed on 24 Aug. 2021.

FIELD

The present invention belongs to the field of chemiluminescence (CL), and relates to a flash-type CL liquid composition based on a $CuInS_2$/ZnS nanomaterial.

BACKGROUND

In recent years, inorganic nanomaterials have been applied widely in the field of electrochemiluminescence because of high quantum efficiency and adjustable band gap, such as CdSe quantum dots (Sens. Actuator B-Chem. 2016, 226, 444-449), CdTe quantum dots (Biosens. Bioelectron. 2019, 131, 178-184), CuInS2 nanomaterial (Anal. Chem. 2018, 90, 3563-3569) and Au cluster (Biosens. Bioelectron. 2021, 190, 113449). However, the reports on inorganic nanomaterials are very limited in the field of direct CL.

The previous patent documents of the inventor of the present invention disclose a method for preparing a $CuInS_2$/ZnS nanomaterial with photoluminescence (PL) and CL characteristics (CN111944521A), and a general method for preparing a carboxylated $CuInS_2$/ZnS nanomaterial with a CL characteristic (CN112940719A). In these documents, CL radiation can be generated in a near-infrared region by taking the $CuInS_2$/ZnS nanomaterial as a chemiluminescent substance and hydrazine hydrate ($N_2H_4.H_2O$) as a triggering reagent. However, if the above-mentioned liquid composition is applied to the field of CL immunoassay, the CL intensity of the liquid composition is far from enough, and the CL time is long, which is not good for rapid analysis.

As a typical flash-type CL representative, the acridinium ester CL liquid composition is CL generated from chemical reaction between acridinium ester and hydrogen peroxide, with high CL intensity and short CL time. However, the synthesis steps of acridinium ester are complicated, a synthesis period is long, and products are easy to decompose under light.

Therefore, it is of great significance to develop a flash-type CL liquid composition with photostability.

SUMMARY

In view of the deficiencies of the prior art, such as cumbersome acridinium ester synthesis steps and easy decomposition of products under light; and low CL intensity and long CL time in the current luminescence liquid composition which uses $CuInS_2$/ZnS nanomaterial as a chemiluminescent substance and hydrazine hydrate as a triggering reagent. The present invention provides a novel flash-type CL liquid composition. In the CL liquid composition, a $CuInS_2$/ZnS nanomaterial is taken as a CL substance, and can generate CL rapidly after being excited by Tris-$N_2H_4.H_2O$—$H_2O_2$, and a CL process (flash-type CL) will end within 1-10 seconds. Further, the CL intensity of the CL liquid composition is greatly improved as compared with the previous CL liquid composition taking the $CuInS_2$/ZnS nanomaterial as a chemiluminescent substance and hydrazine hydrate as a triggering reagent. Compared with acridinium ester (a traditional flash-type chemiluminescent substance), the $CuInS_2$/ZnS nanomaterial is simple in synthesis operation (a one-pot method) and short in the required time, and the synthesized $CuInS_2$/ZnS nanomaterial features good photostability and water solubility, and can generate CL radiation in a near-infrared region.

The technical solution of the present invention is as follows:

A flash-type CL liquid composition based on a $CuInS_2$/ZnS nanomaterial is provided. According to the CL liquid composition, a $CuInS_2$/ZnS nanomaterial as a chemiluminescent substance and a Tris buffer solution containing $N_2H_4.H_2O$ and $H_2O_2$ as an triggering solution form the flash-type CL liquid composition. The CL liquid composition can generate high-intensity flash-type CL signals.

According to the present invention, preferably, a concentration of the Tris in the triggering solution is 0.05-0.2 mol/L, and most preferably 0.1 mol/L.

According to the present invention, preferably, a concentration of the $N_2H_4.H_2O$ in the triggering solution is 5-30 mmol/L, further preferably 10-20 mmol/L, and most preferably 15 mmol/L.

According to the present invention, preferably, a concentration of the $H_2O_2$ in the triggering solution is above 0.01 mol/L, further preferably above 0.5 mol/L, and most preferably 1-2 mol/L.

According to the present invention, preferably, a pH value of the triggering solution is 7-8;

Preferably, the pH value of the triggering solution is adjusted with HCl.

According to the present invention, preferably, the chemiluminescent substance $CuInS_2$/ZnS needs to be centrifugally purified with isopropanol, rapidly and fully dried to remove isopropanol, dissolved in water as much as one-tenth of an original volume of the chemiluminescent substance, then the triggering solution is added to excite the chemiluminescent substance, and a volume ratio of the triggering solution to the original solution is 1:1-5.

According to the present invention, the chemiluminescent substance, i.e., the $CuInS_2$/ZnS nanomaterial, can be synthesized by a one-pot method in the prior art. Preferably, the chemiluminescent substance is prepared from copper chloride, indium chloride, sodium sulfide, zinc acetate and thiourea as raw materials, as well as thiosalicylic acid and sodium citrate as dual ligands by a one-pot method. The resulting $CuInS_2$/ZnS has excellent PL phenomenon, good water solubility and good photostability, with a luminescence wavelength of 660-700 nm.

Most preferably, the $CuInS_2$/ZnS nanomaterial is prepared by the following steps:

(1) weighing 0.024 g of thiosalicylic acid, adding it into a 100 mL three-neck flask, adding 10 mL of deionized water, stirring and dissolving the thiosalicylic acid, and adding 30 mL of deionized water;

(2) adding 800 μL of sodium citrate solution with a concentration of 0.04 mol/L, 2 mL of copper chloride solution with a concentration of 0.01 mol/L and 80 μL of indium trichloride solution with a concentration of 1 mol/L successively to step (1), and stirring the mixed solution for reaction for 5 min;

(3) adding 124 μL of sodium sulfide solution with a concentration of 1 mol/L to step (2), and heating the mixed solution to reflux at 95° C. for 45 min;

(4) adding 4 mL of zinc sulfide solution to step (3), refluxing the mixed solution at 95° C. for 40 min to obtain the nanomaterial, and storing the nanomaterial at 4° C.; wherein the zinc sulfide solution is obtained from reaction between zinc acetate with a concentration of 0.04 mol/L and thiourea with a concentration of 0.04 mol/L, and the pH value is adjusted to 5.7-6.3; and (5) before test, purify the product obtained in step (4) with isopropanol three times, dry the purified product quickly and thoroughly, and dissolve the obtained sample in deionized water as much as one-tenth of an original volume.

According to the present invention, an ultraviolet absorption characteristic peak of the $CuInS_2/ZnS$ nanomaterial is at 500-540 nm, and a PL characteristic peak is at 650-680 nm.

According to the present invention, CL can be generated at the moment of adding the triggering solution into the $CuInS_2/ZnS$ nanomaterial solution, the CL time is generally 1-10 s, and the CL radiation wavelength is in a near-infrared region, i.e., 750-790 nm;

Preferably, the CL intensity of 1 μmol of $CuInS_2/ZnS$ nanomaterial can be above 500 k.

According to the present invention, a method for preparing the triggering solution comprises the following steps:

weighing Tris with a final concentration of 0.1 mol/L, dissolving it in 10 mL of deionized water, adding 0.05-0.2 mmol of $N_2H_4.H_2O$, adjusting the pH value to 7-8 with HCl, and finally adding more than 5 mmol of $H_2O_2$ to obtain the triggering solution.

The principle of the present invention:

The triggering solution of the present invention takes a Tris solution as a buffer solution, $N_2H_4.H_2O$ is added, the pH value is adjusted with HCl, $H_2O_2$ is added, CL can be generated in an instant, and the CL time is generally 1-10 s. The liquid composition belongs to a flash-type CL liquid composition with maximum emission wavelength in a near-infrared region, i.e., 750-790 nm; the CL intensity is high, and the CL intensity of 1 mol of $CuInS_2/ZnS$ nanomaterial can be above 500 k.

The CL liquid composition of the present invention takes the $CuInS_2/ZnS$ nanomaterial as a chemiluminescent substance, exploits the coexisted hydrazine hydrate and $H_2O_2$ as the triggering reagents. Without $H_2O_2$, the $CuInS_2/ZnS$ nanomaterial may react with hydrazine hydrate to generate CL, but the CL emission is very weak and CL process normally lasts over 50 s; these conditions are not favorable for application in the field of chemical immunization. The inventor found that the addition of $H_2O_2$ would greatly enhance the CL reaction between the $CuInS_2/ZnS$ nanomaterial and hydrazine hydrate. Therefore, the CL reaction can be processed rapidly, and all the CL emission can be released within a short time, so that the CL intensity is greatly improved, and the CL liquid composition is transformed from glow-type to flash-type, which is very favorable for application in the field of CL immunoassay.

The beneficial effects of the present invention are as follows:

1. Compared with acridinium ester (a traditional flash-type chemiluminescent substance), the chemiluminescent substance $CuInS_2/ZnS$ nanomaterial of the present invention is extremely simple in the synthesis method, high in the success rate, mild in reaction conditions and short in the required time; a large amount of $CuInS_2/ZnS$ nanomaterial can be synthesized rapidly in a short time.

2. The acridinium ester compound (a traditional flash-type chemical substance) is easy to decompose under light and needs to be stored in a dark place. The chemiluminescent substance $CuInS_2/ZnS$ nanomaterial provided in the present invention has good stability in water and strong photostability, and will not decompose under light.

3. The CL liquid composition of the present invention can generate CL radiation in a near-infrared region, with a maximum emission wavelength of 750-790 nm. The $CuInS_2/ZnS$ nanomaterial is fluorescent in nature, and the fluorescence wavelength is 660-700 nm.

4. In the CL liquid composition provided in the present invention, the addition of $H_2O_2$ can greatly improve the CL emission and shorten the CL process to 1-10 s, making the liquid composition become a typical flash-type CL liquid composition; the flash CL of $CuInS_2/ZnS/N_2H_4.H_2O$—$H_2O_2$ liquid composition can be eye-visible with the $CuInS_2/ZnS$ nanomaterial of 1 μmol level, which is about hundreds times stronger than the glow-CL of $CuInS_2/ZnS/N_2H_4.H_2O$ liquid composition under the same concentration condition.

5. The CL liquid composition of the present invention can generate high-intensity flash-type CL under a physiological condition, and has good application prospect in the aspect of biological rapid detection.

DETAILED DESCRIPTION OF THE PREFERRED EMBODIMENTS

The present invention will be further described below through, but not limited to, embodiments.

The mass fraction of $N_2H_4.H_2O$ used in the embodiment of the present invention is 50%, and the mass fraction of $H_2O_2$ is 30%.

A PL (fluorescence) spectrum of the $CuInS_2/ZnS$ nanomaterial prepared in the embodiment was collected and obtained by an F-320 fluorescence spectrophotometer manufactured by Tianjin Gangdong Sci & Tech. Development Co., Ltd., and the triggering wavelength was 540 nm. The UV-vis absorption spectrum was collected and obtained by a TU-1901 UV-vis spectrophotometer manufactured by Beijing Purkinje General Instrument Co., Ltd. The CL spectrum was collected and obtained by a CCD grating spectrometer manufactured by Princeton Instruments. This instrument is composed of an Acton SP2300i monochrometer and a PyLoN400BReXcelon CCD detector, and the CL spectrum collection time is 10 s.

Comparative Example 1

A $CuInS_2/ZnS$ nanomaterial coated with double stabilizers of thiosalicylic acid and sodium citrate was synthesized by the following specific steps:
(1) 0.024 g of thiosalicylic acid was weighed and added into a 100 mL three-neck flask, 10 mL of deionized water was added, the solution was stirred, the thiosalicylic acid was dissolved, and 30 mL of deionized water was added;
(2) 800 μL of sodium citrate solution with a concentration of 0.04 mol/L, 2 mL of copper chloride solution with a concentration of 0.01 mol/L and 80 μL of indium trichloride solution with a concentration of 1 mol/L were added successively to step (1), and the mixed solution was stirred for the reaction for 5 min;
(3) 124 μL of sodium sulfide solution with a concentration of 1 mol/L was added to step (2), and the mixed solution was heated to reflux at 95° C. for 45 min; and
(4) 4 mL of zinc sulfide solution was added to step (3), the mixed solution was refluxed at 95° C. for 40 min to obtain the nanomaterial, and the nanomaterial was stored at 4° C.

The zinc sulfide solution was obtained from reaction between zinc acetate with a concentration of 0.04 mol/L and thiourea with a concentration of 0.04 mol/L, and the pH value was adjusted to 5.7-6.3. Then the $CuInS_2/ZnS$ nanomaterial was obtained.

Figure 1:
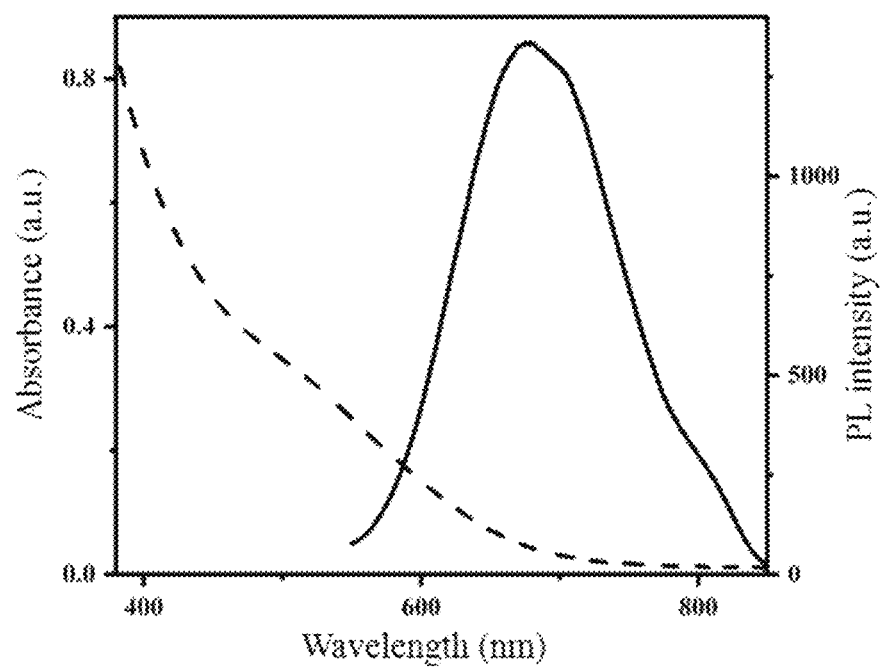
FIG. 1 is a fluorescence spectrum and UV-vis absorption spectrum of the $CuInS_2/ZnS$ nanomaterial prepared in comparative example 1.

The fluorescence spectrum and UV-vis absorption spectrum of the $CuInS_2/ZnS$ nanomaterial obtained are as shown in FIG. 1, wherein the solid line is a fluorescence spectrum curve, and the dotted line is a UV-vis spectrum curve. FIG. 1 shows that an ultraviolet absorption characteristic peak of the $CuInS_2/ZnS$ nanomaterial is at 500-540 nm, a fluorescence wavelength is at 650-680 nm, the Stokes shift is large, which is consistent with the characteristics of group I-III-VI quantum dots.

Figure 4:
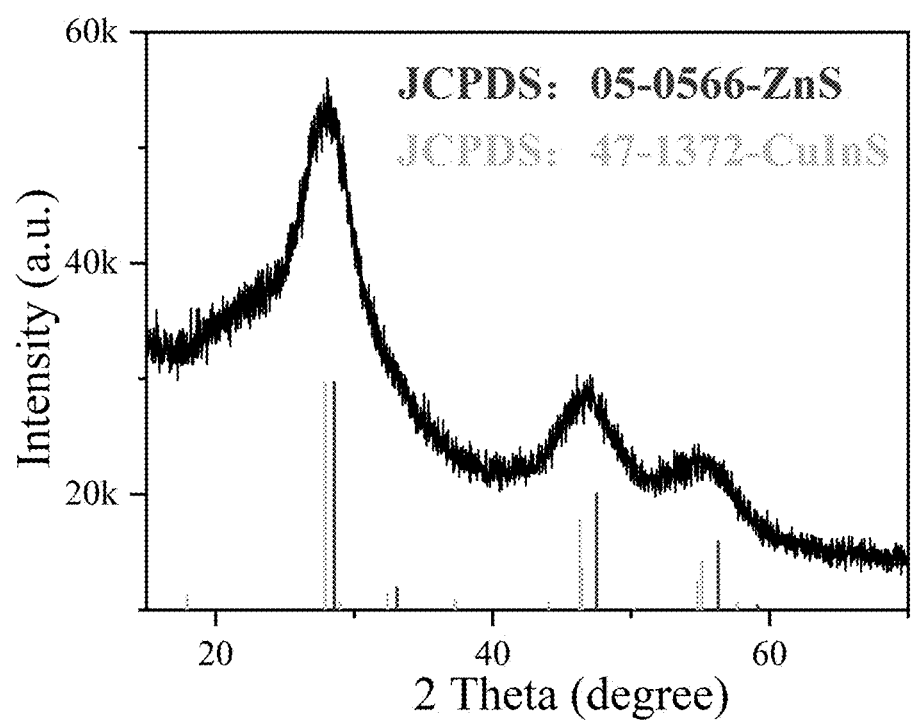
FIG. 4 is an XRD pattern of the $CuInS_2/ZnS$ nanomaterial prepared in comparative example 1.
Figure 5:
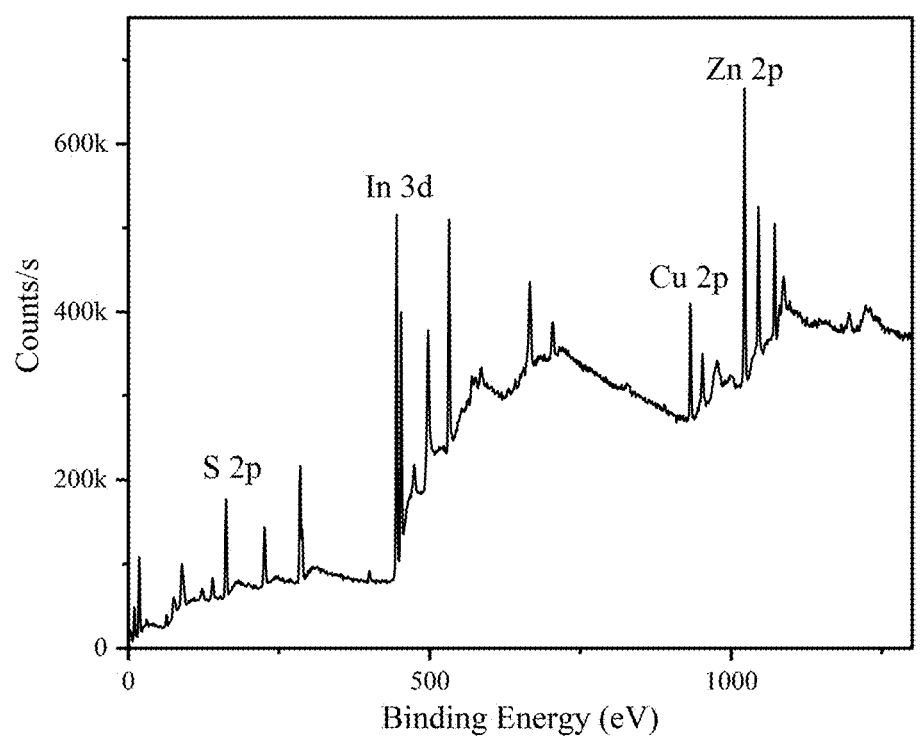
FIG. 5 is an XPS pattern of the $CuInS_2/ZnS$ nanomaterial prepared in comparative example 1.

The XRD pattern of the $CuInS_2/ZnS$ nanomaterial is as shown in FIG. 4, the XPS pattern is as shown in FIG. 5.

An triggering solution-1 was prepared by the following specific steps: 0.1211 g of Tris was weighed and dissolved in 10 mL of deionized water, 10 μL of $N_2H_4.H_2O$ was added, and the pH value was adjusted to 7 with HCl.

300 L of $CuInS_2/ZnS$ nanomaterial was taken, placed in a centrifuge tube, centrifugally purified with isopropanol three times and rapidly dried by an air blower to remove isopropanol, the precipitate was dissolved in 30 μL of deionized water, the solution was taken out and placed in a sample cell, 300 μL of triggering solution-1 was rapidly injected, and a CL signal was collected.

Figure 2:
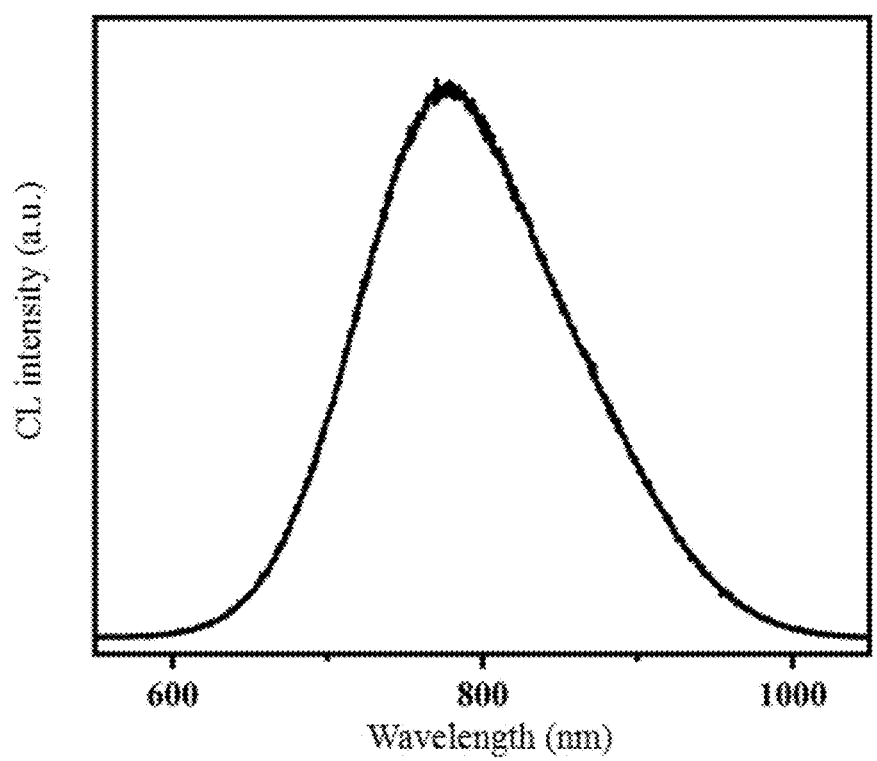
FIG. 2 is a CL spectrum of the $CuInS_2/ZnS$ nanomaterial and triggering solution-1 prepared in comparative example 1.

The CL spectrum of the $CuInS_2/ZnS$ nanomaterial and the triggering solution-1 is as shown in FIG. 2. It can be known from FIG. 2 that the CL characteristic peak is at 780-820 nm.

Figure 3:
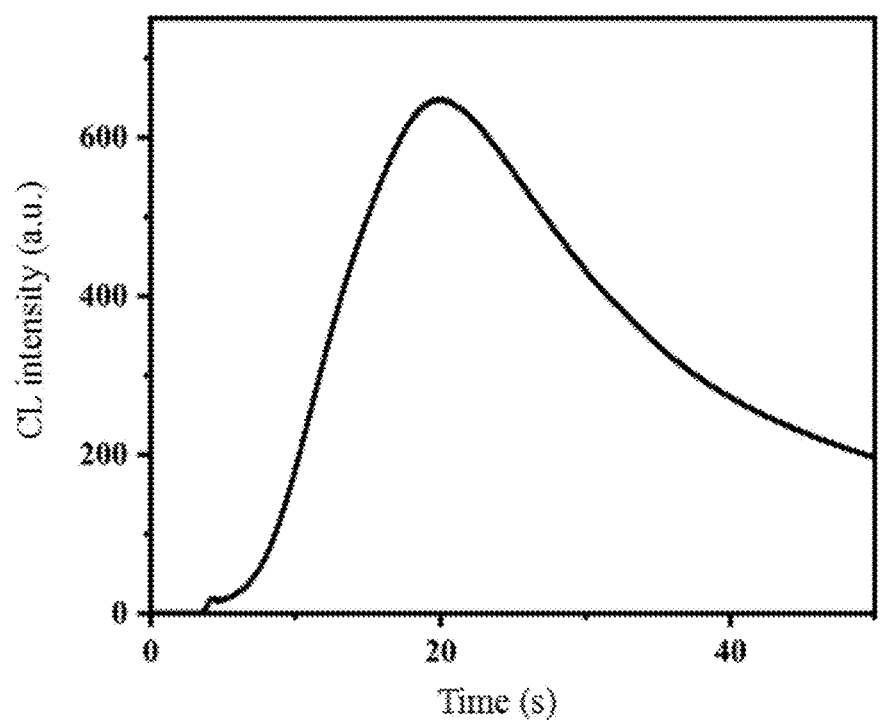
FIG. 3 is a CL intensity curve of the $CuInS_2/ZnS$ nanomaterial and triggering solution-1 prepared in comparative example 1.

The CL intensity curve of the $CuInS_2/ZnS$ nanomaterial and the triggering solution-1 is as shown in FIG. 3. It can be known from FIG. 3 that the CL intensity of the CL liquid composition containing 1 μmol of $CuInS_2/ZnS$ nanomaterial is 600-700, and the CL time is above 50 s.

Example 1

The preparation steps of the $CuInS_2/ZnS$ nanomaterial are the same as that in comparative example 1.

An triggering solution-2 was prepared by the following specific steps: 0.1211 g of Tris was weighed and dissolved in 8.5 mL of deionized water, 11.8 μL of $N_2H_4.H_2O$ was added, the pH value was adjusted to 7 with HCl, and 1.5 mL of $H_2O_2$ was added.

1 μmol of $CuInS_2/ZnS$ nanomaterial was taken, placed in a centrifuge tube, centrifugally purified with isopropanol three times and rapidly dried by an air blower to remove isopropanol, the precipitate was dissolved in 30 μL of deionized water, the solution was taken out and placed in a sample cell, 300 μL of triggering solution-2 was rapidly injected, and a CL signal was collected.

Example 2

The steps are the same as those in example 1, and the difference lies in the triggering solution:

An triggering solution-3 was prepared by the following specific steps: 0.1211 g of Tris was weighed and dissolved in 8.5 mL of deionized water, 5.9 μL of $N_2H_4.H_2O$ was added, the pH value was adjusted to 7 with HCl, and 1.5 mL of $H_2O_2$ was added.

Figure 6:
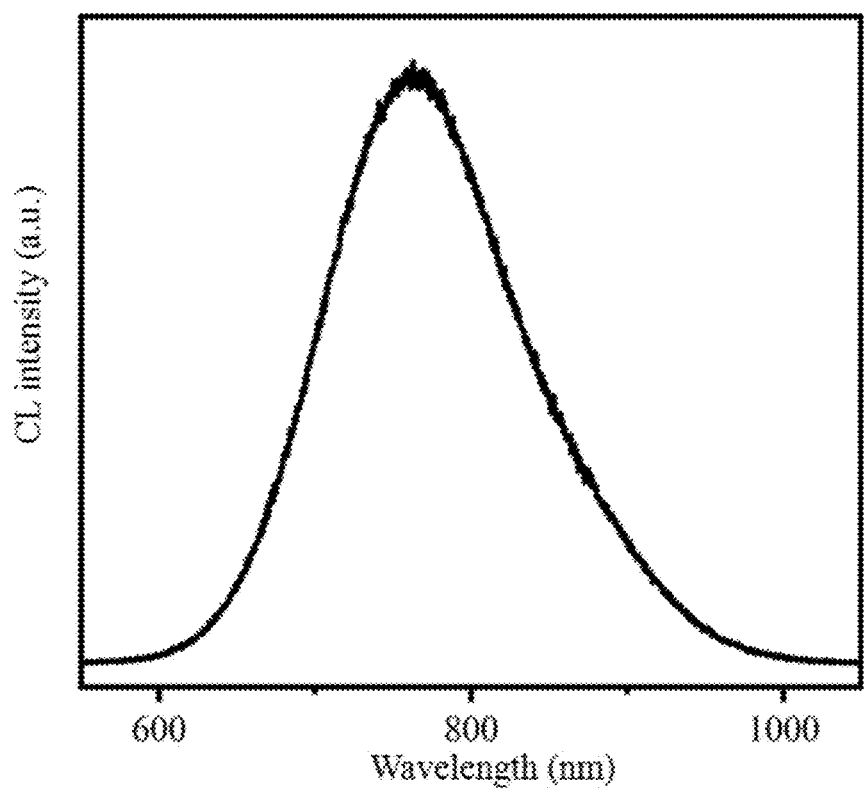
FIG. 6 is a CL spectrum of the $CuInS_2/ZnS$ nanomaterial and an triggering solution-2 prepared in example 1.

The CL spectrum of the $CuInS_2/ZnS$ nanomaterial and the triggering solution-2 in this example is as shown in FIG. 6. It can be known from FIG. 6 that the CL radiation wavelength of the CL liquid composition is in a near-infrared region, i.e., 750-790 nm.

Figure 7:
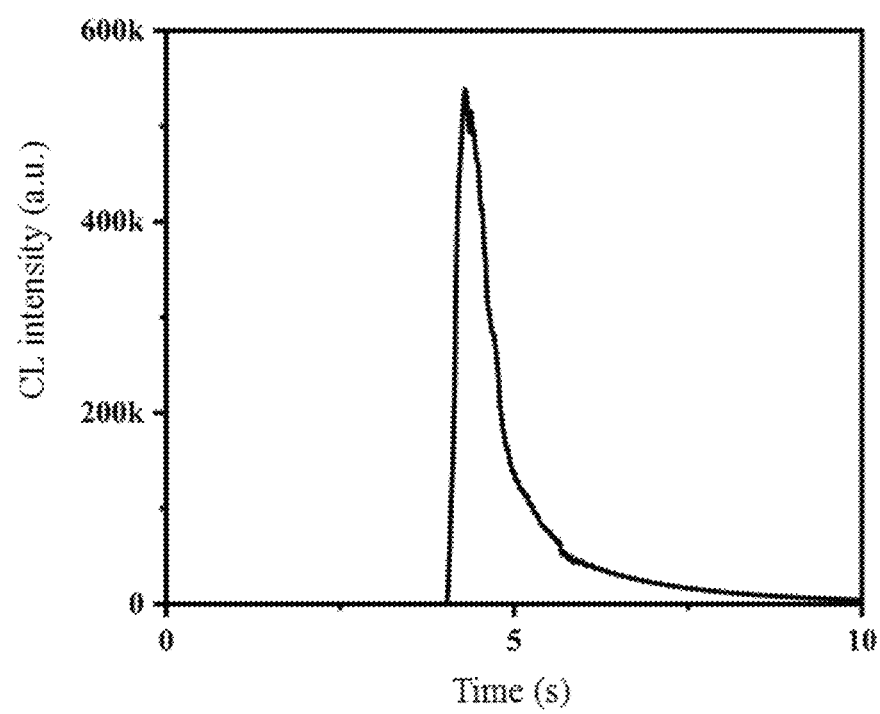
FIG. 7 is a CL intensity curve of the $CuInS_2/ZnS$ nanomaterial and the triggering solution-2 prepared in example 1.

The CL intensity curve of the $CuInS_2/ZnS$ nanomaterial and the triggering solution-2 in this embodiment is as shown in FIG. 7. It can be known from FIG. 7 that the CL intensity of the CL liquid composition containing 1 μmol of $CuInS_2/ZnS$ nanomaterial is above 500 k, which is more than 800 times as much as that of a liquid composition without $H_2O_2$, the CL time is 2-5 s, and the CL liquid composition belongs to a flash-type luminescence liquid composition.

Example 3

The steps are the same as those in example 1, and the difference lies in the triggering solution:

An triggering solution-4 was prepared by the following specific steps: 0.1211 g of Tris was weighed and dissolved in 8.5 mL of deionized water, 17.7 μL of $N_2H_4.H_2O$ was added, the pH value was adjusted to 7 with HCl, and 1.5 mL of $H_2O_2$ was added.

Example 4

The steps are the same as those in example 1, and the difference lies in the triggering solution:

An triggering solution-5 was prepared by the following specific steps: 0.1211 g of Tris was weighed and dissolved in 8.5 mL of deionized water, 23.6 μL of $N_2H_4.H_2O$ was added, the pH value was adjusted to 7 with HCl, and 1.5 mL of $H_2O_2$ was added.

Example 5

The steps are the same as those in example 1, and the difference lies in the triggering solution:

An triggering solution-6 was prepared by the following specific steps: 0.1211 g of Tris was weighed and dissolved in 8.5 mL of deionized water, 35.4 μL of $N_2H_4 \cdot H_2O$ was added, the pH value was adjusted to 7 with HCl, and 1.5 mL of $H_2O_2$ was added.

Example 6

The steps are the same as those in example 1, and the difference lies in the triggering solution:

An triggering solution-7 was prepared by the following specific steps: 0.1211 g of Tris was weighed and dissolved in 9.985 mL of deionized water, 11.8 μL of $N_2H_4 \cdot H_2O$ was added, the pH value was adjusted to 7 with HCl, and 0.015 mL of $H_2O_2$ was added.

Example 7

The steps are the same as those in example 1, and the difference lies in the triggering solution:

An triggering solution-8 was prepared by the following specific steps: 0.1211 g of Tris was weighed and dissolved in 9.85 mL of deionized water, 10.2 μL of $N_2H_4 \cdot H_2O$ was added, the pH value was adjusted to 7 with HCl, and 0.15 mL of $H_2O_2$ was added.

Example 8

The steps are the same as those in example 1, and the difference lies in the triggering solution:

An triggering solution-9 was prepared by the following specific steps: 0.1211 g of Tris was weighed and dissolved in 9.25 mL of deionized water, 10.9 μL of $N_2H_4 \cdot H_2O$ was added, the pH value was adjusted to 7 with HCl, and 0.75 mL of $H_2O_2$ was added.

Example 9

The steps are the same as those in example 1, and the difference lies in the triggering solution:

An triggering solution-10 was prepared by the following specific steps: 0.1211 g of Tris was weighed and dissolved in 7 mL of deionized water, 13.6 μL of $N_2H_4 \cdot H_2O$ was added, the pH value was adjusted to 7 with HCl, and 3 mL of $H_2O_2$ was added.

Example 10

The steps are the same as those in example 1, and the difference lies in the triggering solution:

An triggering solution-11 was prepared by the following specific steps: 0.1211 g of Tris was weighed and dissolved in 8.5 mL of deionized water, 11.8 μL of $N_2H_4 \cdot H_2O$ was added, the pH value was adjusted to 6 with HCl, and 1.5 mL of $H_2O_2$ was added.

Example 11

The steps are the same as those in example 1, and the difference lies in the triggering solution:

An triggering solution-12 was prepared by the following specific steps: 0.1211 g of Tris was weighed and dissolved in 8.5 mL of deionized water, 11.8 μL of $N_2H_4 \cdot H_2O$ was added, the pH value was adjusted to 8 with HCl, and 1.5 mL of $H_2O_2$ was added.

Example 12

The steps are the same as those in example 1, and the difference lies in the triggering solution:

An triggering solution-13 was prepared by the following specific steps: 0.1211 g of Tris was weighed and dissolved in 8.5 mL of deionized water, 11.8 μL of $N_2H_4 \cdot H_2O$ was added, the pH value was adjusted to 9 with HCl, and 1.5 mL of $H_2O_2$ was added.

Test Example 1

Figure 8:
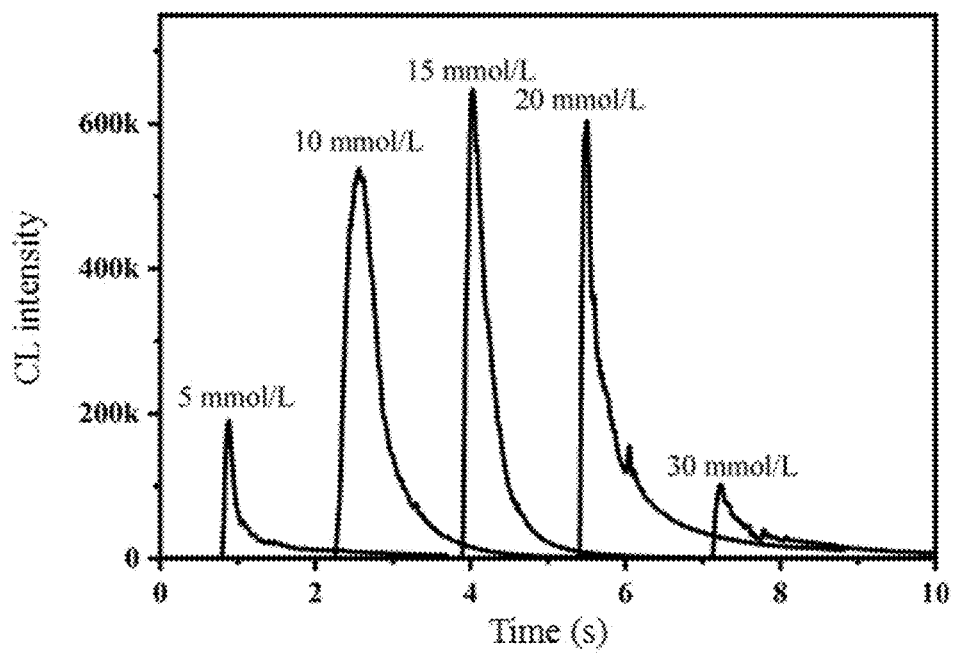
FIG. 8 is a comparison diagram of the CL intensities generated by the $CuInS_2/ZnS$ nanomaterial and corresponding triggering solutions prepared in examples 1, 2, 3, 4 and 5.

A comparison diagram of the CL intensities generated by the $CuInS_2/ZnS$ nanomaterial and corresponding triggering solutions prepared in examples 1, 2, 3, 4 and 5 is as shown in FIG. 8. It can be known from FIG. 9 that when a concentration of $N_2H_4 \cdot H_2O$ in the triggering solution is 10-20 mmol/L under the same conditions, the CL intensity is high, which is above 530 k.

Test Example 2

Figure 9:
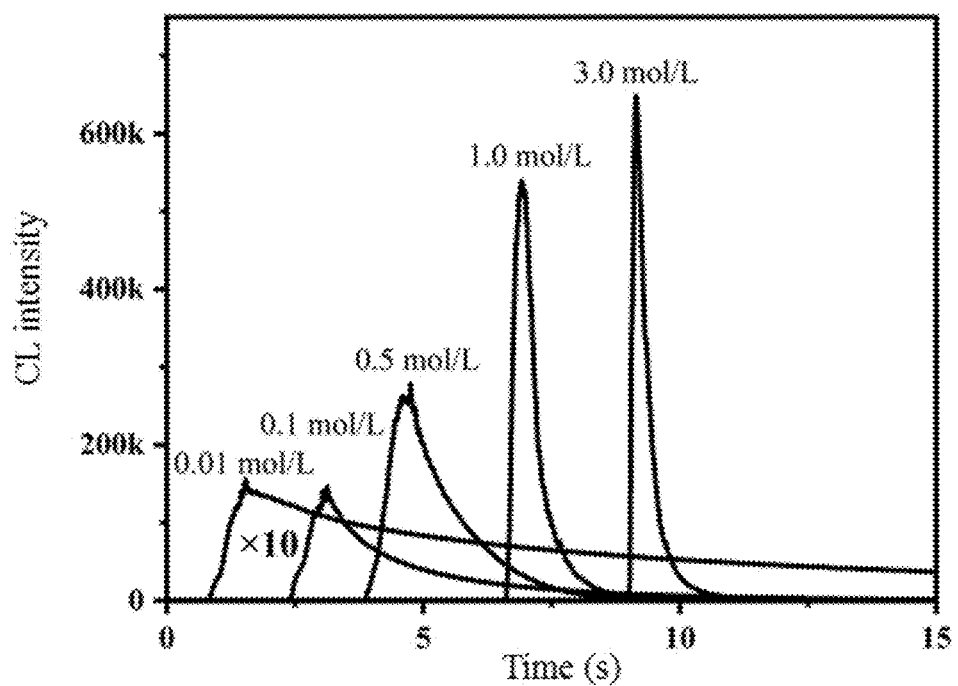
FIG. 9 is a comparison diagram of the CL intensities generated by the $CuInS_2/ZnS$ nanomaterial and corresponding triggering solutions prepared in examples 1, 6, 7, 8 and 9.

A comparison diagram of the CL intensities generated by the $CuInS_2/ZnS$ nanomaterial and corresponding triggering solutions prepared in examples 1, 6, 7, 8 and 9 is as shown in FIG. 9. It can be known from FIG. 10 that when a concentration of $H_2O_2$ in the triggering solution is 1-2 mol/L under the same conditions, the CL intensity is high, which is above 530 k.

Test Example 3

Figure 10:
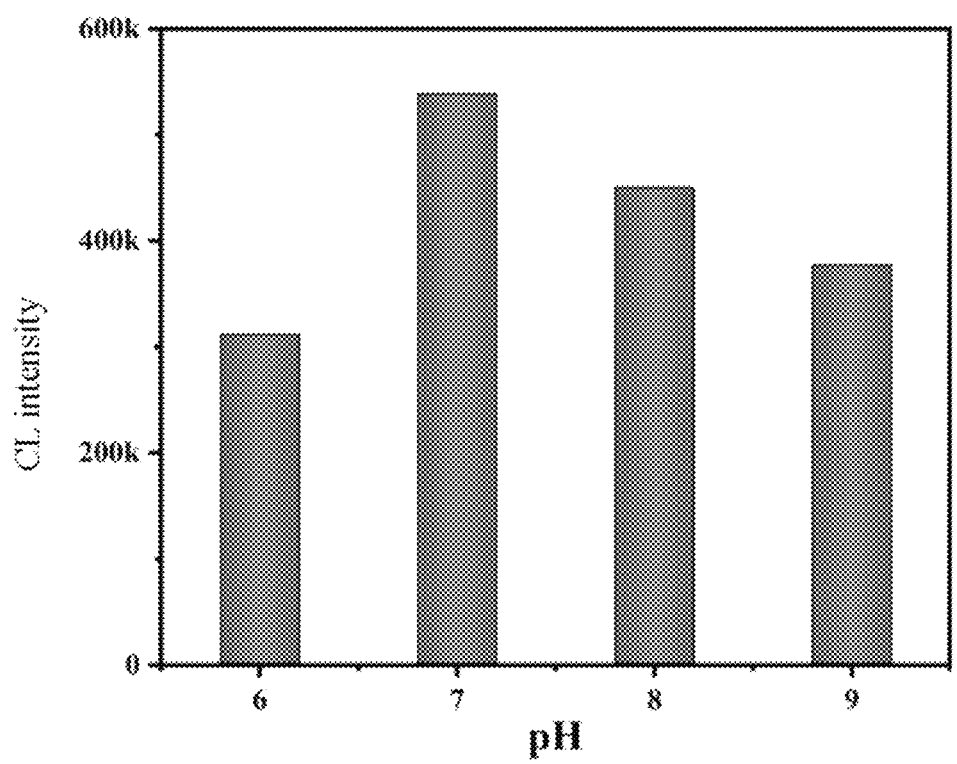
FIG. 10 is a comparison diagram of the CL intensities generated by the $CuInS_2/ZnS$ nanomaterial and corresponding triggering solutions prepared in examples 1, 10, 11 and 12.

A comparison diagram of the CL intensities generated by the $CuInS_2/ZnS$ nanomaterial and corresponding triggering solutions prepared in examples 1, 10, 11 and 12 is as shown in FIG. 10. It can be known from FIG. 11 that when the pH value of the triggering solution is 7-8 under the same conditions, the CL intensity is high, which is above 450 k.

What is claimed is:

1. A flash-type chemiluminescence (CL) liquid composition based on a $CuInS_2/ZnS$ nanomaterial, wherein a $CuInS_2/ZnS$ nanomaterial as a chemiluminescent luminophore and a Tris buffer solution containing hydrazine hydrate and $H_2O_2$ as the triggering solution form the flash-type CL liquid composition, wherein a concentration of the hydrazine hydrate in the triggering solution is 5-30 mmol/L, wherein a concentration of the $H_2O_2$ in the triggering solution is above 0.01 mol/L, wherein a pH value of the triggering solution is 6-9.

2. The flash-type CL liquid composition based on a $CuInS_2/ZnS$ nanomaterial according to claim 1, wherein a concentration of the Tris in the triggering solution is 0.05-0.2 mol/L.

3. The flash-type CL liquid composition based on a $CuInS_2/ZnS$ nanomaterial according to claim 1, wherein a concentration of the $N_2H_4 \cdot H_2O$ in the triggering solution is 10-20 mmol/L.

4. The flash-type CL liquid composition based on a $CuInS_2/ZnS$ nanomaterial according to claim 1, wherein a concentration of the $H_2O_2$ in the triggering solution is 1-2 mol/L.

5. The flash-type CL liquid composition based on a $CuInS_2/ZnS$ nanomaterial according to claim 1, wherein a pH value of the triggering solution is 7-8.

6. The flash-type CL liquid composition based on a $CuInS_2/ZnS$ nanomaterial according to claim 1, wherein the chemiluminescent substance $CuInS_2/ZnS$ is centrifugally purified with isopropanol, dried to remove isopropanol and dissolved in water as much as one-tenth of an original volume of the chemiluminescent substance, then the triggering solution is added to excite the chemiluminescent substance, and a volume ratio of the triggering solution and the original solution is 1:1-5.

7. The flash-type CL liquid composition based on a $CuInS_2/ZnS$ nanomaterial according to claim 1, wherein a CL time of the flash-type CL liquid composition based on a $CuInS_2/ZnS$ nanomaterial is 1-10 s, and a CL radiation wavelength is 750-790 nm.

8. The flash-type CL liquid composition based on a $CuInS_2/ZnS$ nanomaterial according to claim 1, wherein the triggering solution is prepared according to the following steps:

weighing Tris with a final concentration of 0.1 mol/L in 10 mL of deionized water, adding 0.05-0.2 mmol of hydrazine hydrate, adjusting the pH value to 7-8 with HCl, and finally adding more than 5 mmol of $H_2O_2$ to obtain the triggering solution.

\* \* \* \* \*